(12) United States Patent
Zeng et al.

(10) Patent No.: US 7,504,443 B2
(45) Date of Patent: Mar. 17, 2009

(54) DENTAL ADHESIVE COMPOSITION

(75) Inventors: Weiping Zeng, Moriyama (JP); Akari Shimozono, Moriyama (JP)

(73) Assignee: Sun Medical Co., Ltd. (JP)

( * ) Notice: Subject to any disclaimer, the term of this patent is extended or adjusted under 35 U.S.C. 154(b) by 371 days.

(21) Appl. No.: 10/523,027

(22) PCT Filed: Sep. 30, 2003

(86) PCT No.: PCT/JP03/12503

§ 371 (c)(1), (2), (4) Date: Feb. 2, 2005

(87) PCT Pub. No.: WO2004/047773

PCT Pub. Date: Jun. 10, 2004

(65) Prior Publication Data

US 2005/0256221 A1    Nov. 17, 2005

(30) Foreign Application Priority Data

Nov. 22, 2002    (JP) .............................. 2002-339196

(51) Int. Cl.
*A61K 6/08* (2006.01)
*A61K 6/083* (2006.01)
*A61K 6/00* (2006.01)
*C08F 4/12* (2006.01)
*C08F 4/52* (2006.01)
*C07F 5/02* (2006.01)
*A61C 5/00* (2006.01)

(52) U.S. Cl. ....................... 523/116; 523/118; 526/195; 526/196; 568/7; 433/228.1

(58) Field of Classification Search ................. 523/115, 523/116, 118; 526/195, 196; 568/7; 433/228.1
See application file for complete search history.

(56) References Cited

U.S. PATENT DOCUMENTS

| 5,147,903 | A | * | 9/1992 | Podszun et al. ............. 523/115 |
| 5,171,763 | A | | 12/1992 | Ohno et al. |
| 5,700,875 | A | * | 12/1997 | Zeng et al. .................. 525/301 |
| 5,925,690 | A | * | 7/1999 | Fuchigami et al. .......... 523/118 |
| 6,027,813 | A | * | 2/2000 | Deviny ...................... 428/422 |
| 6,037,388 | A | * | 3/2000 | Hashimoto et al. ......... 523/118 |
| 6,051,626 | A | * | 4/2000 | Zeng et al. .................. 523/118 |
| 6,353,039 | B1 | * | 3/2002 | Rheinberger et al. ........ 523/109 |
| 6,413,698 | B1 | * | 7/2002 | Tamura et al. ........... 430/284.1 |
| 6,437,065 | B1 | * | 8/2002 | Ritter et al. ................ 526/227 |

FOREIGN PATENT DOCUMENTS

| EP | 0 758 544 | 2/1997 |
| JP | 06-227934 | 8/1994 |
| JP | 110913/1997 | 4/1997 |
| JP | 10-236912 | 9/1998 |
| JP | 10-338611 | 12/1998 |

* cited by examiner

*Primary Examiner*—Mark Eashoo
*Assistant Examiner*—Michael Pepitone
(74) *Attorney, Agent, or Firm*—H. Jay Spiegel; Robert L. Haines

(57) ABSTRACT

The dental adhesive composition of the present invention comprises a polyfunctional polymerizable monomer which is an ester compound of a polyhydric alcohol of 3 to 6 carbon atoms and plural (meth)acrylic acids and has 1 to 2 hydroxyl groups, a monofunctional (meth)acrylate having no hydroxyl group in its molecule, a polymerizable monomer containing an acid group in its molecule, an organoboron compound as a curing agent and a filler. According to the present invention, a dental adhesive composition remarkably enhanced in the curing rate with rarely affecting adhesion properties of the composition, working time and flexibility of a cured product is provided.

16 Claims, No Drawings

DENTAL ADHESIVE COMPOSITION

TECHNICAL FIELD

The present invention relates to dental adhesive materials, and more particularly to dental adhesive compositions such as dental bonding materials and dental resin cements.

BACKGROUND ART

In the dental treatments, it is necessary to bond treatment restorative materials to dentin or restorative materials. Important properties of adhesive compositions used for adhesion bonding are, for example, adhesion properties enough for withstanding oral cavity conditions, mechanical properties (e.g., flexibility) of cured products and favorable workability (e.g., proper setting time (curing time) and working time), capable of coping with applied cases.

It has been confirmed from the long-term clinical use that adhesives using as a polymerization initiator a partial oxide of tributylborane (TBB-O) that is an organoboron compound, e.g., a methyl methacrylate (MMA)/4-methacryloyloxyethyltrimellitic anhydride (4-META/partial oxide of tributylborane (TBB-O)/polymethyl methacrylate (PMMA) adhesive resin, not only have excellent adhesion properties but also are less bio-harmful. Such adhesive resins, however, have relatively low curing rate, and it has been pointed out that a relatively long period of time is necessary before the resins exhibit satisfactory adhesion performance, so that shortening of the setting time has been desired. However, it cannot be said that the shorter the setting time is, the better the dental adhesive compositions are, and it is preferable that the compositions are cured rapidly after the elapse of working time necessary for the dental treatment.

The present inventor has found that by the use of a polymerization initiation system comprising an organoboron compound and an appropriately small amount of a photopolymerization initiator, the curing rate can be controlled without exerting evil influences on the adhesion properties of an adhesive composition, and he has already applied for patent. This application has been already laid open (Japanese Patent Laid-Open Publication No. 110913/1997).

In the adoption of this polymerization system, however, an additional operation that light energy must be given by a certain means is required in order to control the curing rate by the use of an appropriately small amount of a photopolymerization initiator.

Under such circumstances, a basic solution to provide favorable workability with a proper setting time has been desired in the field of dental treatments.

The present inventor has studied such requirements as mentioned above, and as a result, he has found that by the addition of a small amount of a polyfunctional polymerizable monomer which is an ester compound of a polyhydric alcohol of 3 to 6 carbon atoms and plural (meth)acrylic acids and has 1 to 2 hydroxyl groups to a composition, the curing rate can be remarkably enhanced with rarely affecting adhesion properties of the composition, properties of a cured product and working time. Based on the finding, the present invention has been accomplished.

Patent document 1: Japanese Patent Laid-Open Publication No. 110913/1997

OBJECT OF THE INVENTION

It is an object of the present invention to provide an adhesive composition having excellent adhesion properties and excellent workability in the dental treatments.

DISCLOSURE OF THE INVENTION

The dental adhesive composition of the present invention comprises:

(A) a polyfunctional polymerizable monomer which is an ester compound of a polyhydric alcohol of 3 to 6 carbon atoms and plural (meth)acrylic acids and has 1 to 2 hydroxyl groups, in an amount of 1 to 30 parts by weight, (B) a monofunctional (meth)acrylate in an amount of 65 to 95 parts by weight, (C) a polymerizable monomer having an acid group, in an amount of 1 to 10 parts by weight, and (D) an organoboron compound in an amount of 0.5 to 10 parts by weight based on 100 parts by weight of the total of the polyfunctional polymerizable monomer (A), the monofunctional (meth)acrylate (B) and the polymerizable monomer (C) having an acid group, with the proviso that the total of the component (A), the component (B) and the component (C) is 100 parts by weight.

The dental adhesive composition preferably further comprises:

(E) a filler, and/or (F) a solvent.

By combining a polymerizable monomer having a specific structure with a curing agent as described above, the setting time can be shortened without affecting adhesion properties, working time and properties of the composition.

EFFECT OF THE INVENTION

By the addition of a small amount of a polyfunctional polymerizable monomer having a specific structure, namely, a polyfunctional polymerizable monomer which is an ester compound of a polyhydric alcohol of 3 to 6 carbon atoms and plural (meth)acrylic acids and has 1 to 2 hydroxyl groups, to a dental adhesive composition, the curing rate can be remarkably enhanced with rarely affecting adhesion properties of the composition, properties of a cured product and working time.

BEST MODE FOR CARRYING OUT THE INVENTION

The dental adhesive composition of the invention is described in detail hereinafter.

The polyfunctional polymerizable monomer (A) having 1 to 2 hydroxyl groups for use in the invention is an ester compound of a polyhydric alcohol of 3 to 6 carbon atoms and plural acrylic acids and/or methacrylic acids.

The polyfunctional polymerizable monomer (A) has plural functional groups. These functional groups are usually derived from ethylenically unsaturated bonds, and they are usually acrylic groups or methacrylic groups introduced by esterification reaction with a polyhydric alcohol.

Examples of the polyhydric alcohols of 3 to 6 carbon atoms for forming the ester compound include glycerol, butanetriol, butanetetraol, pentanetriol, pentanetetraol, xylitol, hexanetriol, hexanetetraol, hexanepentaol and hexanehexaol.

The polyfunctional polymerizable monomer (A) for use in the invention is a partial ester compound of such a polyhydric alcohol as mentioned above and acrylic acids and/or methacrylic acids, and in this compound, 1 to 2 hydroxyl groups remain.

Examples of the polyfunctional polymerizable monomers (A) include glycerol di(meth)acrylate; di(meth)acrylates of butanetriol, such as trimethylolpropane; di(meth)acrylates or tri(meth)acrylates of butanetetraol, such as meso-erythritol; di(meth)acrylates of pentanetriol; di(meth)acrylates or tri (meth)acrylates of pentanetetraol, such as tetramethylolmethane; polyfunctional (meth)acrylates having 1 to 2 hydroxyl groups of xylitol or its isomers; di(meth)acrylates of hexanetriol; di(meth)acrylates or tri(meth)acrylates of hexanetetraol; polyfunctional (meth)acrylates having 1 to 2 hydroxyl groups of hexanepentaol; and polyfunctional (meth)acrylates having 1 to 2 hydroxyl groups of hexanehexaol. Of these, polyfunctional (meth)acrylates having 2 to 3 functional groups are preferably employed, and polyfunctional (meth)acrylates having 2 functional groups are more preferably employed. If the number of functional groups is large, the degree of crosslinking of a cured product of the composition is increased though it depends upon the amount added. Hence, flexibility of the cured product of the composition is impaired, and adhesion properties to dentin or dental metals tend to be decreased.

In the dental adhesive composition of the invention, the polyfunctional polymerizable monomer which is an ester compound of a polyhydric alcohol of 3 to 6 carbon atoms and plural (meth)acrylic acids and has 1 to 2 hydroxyl groups is contained in an amount of 1 to 30 parts by weight, preferably 1 to 20 parts by weight, most preferably 2 to 9 parts by weight, in 100 parts by weight of the total of the polyfunctional polymerizable monomer (A), the monofunctional (meth) acrylate (B) and the polymerizable monomer (C) having an acid group for forming the dental adhesive composition of the invention. If the amount of the polyfunctional polymerizable monomer (A) is small, an effect of acceleration of curing rate is small. If the amount of the polyfunctional polymerizable monomer (A) is large, the setting time becomes too short, and therefore, the time to properly carry out the dental treatment tends to be decreased, or water absorption capacities of a cured product of the composition are increased, whereby retention of adhesion to metals or dentin tends to be decreased. Further, the degree of crosslinking of a cured product of the composition is increased, and hence, flexibility of the cured product of the composition tends to be impaired.

The monofunctional (meth)acrylate (B) for use in the invention is a monofunctional (meth)acrylate having no hydroxyl group in its molecule.

Examples of the monofunctional (meth)acrylates (B) include:

alkyl (meth)acrylates, such as methyl (meth)acrylate, ethyl (meth)acrylate, propyl (meth)acrylate, hexyl (meth)acrylate, 2-ethylhexyl-(meth)acrylate, dodecyl (meth)acrylate, lauryl (meth)acrylate, cyclohexyl (meth)acrylate, benzyl (meth) acrylate and isobornyl (meth)acrylate;

(poly)alkylene glycol monoalkyl ether (meth)acrylates, such as ethylene glycol monomethyl ether (meth)acrylate, ethylene glycol monoethyl ether (meth)acrylate, diethylene glycol monomethyl ether (meth)acrylate, triethylene glycol monomethyl ether (meth)acrylate, polyethylene glycol monomethyl ether (meth)acrylate and polypropylene glycol monoalkyl ether (meth)acrylate;

fluoroalkyl esters of (meth)acrylic acids, such as perfluorooctyl (meth)acrylate and hexafluoro(meth)acrylate;

silane compounds having (meth)acryloxyalkyl groups, such as γ-(meth)acryloxypropyltri(trimethylsiloxy)silane; and (meth)acrylates having heterocyclic rings, such as tetrahydrofurfuryl (meth)acrylate.

In order to obtain high bond strength to dentin or the like, a low-molecular weight monomer capable of being diffused into an adhesive surface of dentin or the like, e.g., a low-molecular weight monomer having a molecular weight of not more than 300, is useful. Examples of such low-molecular weight monomers include methyl methacrylate, ethyl methacrylate, propyl methacrylate and ethylene glycol monomethyl ether (meth)acrylate. In the present invention, the low-molecular weight monomer is also available as the monofunctional (meth)acrylate (B).

The monofunctional polymerizable monomers mentioned above can be used singly or in combination.

In the present invention, a methacrylate which is relatively lowly irritant to human body is particularly preferably used as the monofunctional (meth)acrylate (B).

In the composition of the invention, the monofunctional (meth)acrylate (B) is contained in an amount of 65 to 95 parts by weight, preferably 75 to 94 parts by weight, particularly preferably 80 to 93 parts by weight, in 100 parts by weight of the total of the polyfunctional polymerizable monomer (A), the monofunctional (meth)acrylate (B) and the polymerizable monomer (C) having an acid group for forming the dental composition of the invention. The monofunctional (meth) acrylate (B) is a monomer that is a base monomer to allow excellent properties of the dental adhesive composition of the invention to appear, and by the use of this monomer in the above amount, the basic properties of the dental adhesive composition of the invention are established.

The polymerizable monomer (C) containing an acid group in its molecule, which is used in the invention, has a function of enhancing adhesion properties to dentin or the like, and the acid group of the polymerizable monomer (C) is, for example, a carboxyl group, a carboxylic anhydride group, a phosphoric acid group or a sulfonic acid group.

Examples of polymerizable monomers having a carboxyl group in a molecule, which are employable as the polymerizable monomers (C) containing an acid group in a molecule, include monocarboxylic acids, dicarboxylic acids, tricarboxylic acids, tetracarboxylic acids and their derivatives. More specifically, there can be mentioned, for example, (meth)acrylic acid, maleic acid, p-vinylbenzoic acid, 2-(meth)acryloyloxyethylsuccinic acid, 11-(meth)acryloyloxy-1,1-undecanedicarboxylic acid (in case of methacrylate: MAC-10 (trade name)), 1,4-di(meth)acryloyloxyethylpyromellitic acid, 6-(meth)acryloyloxyethyltrimellitic acid and its anhydride, 4-(meth)acryloyloxyethyltrimellitic acid (in case of methacrylate: 4-MET) and its anhydride (in case of methacrylate: 4-META), 4-(meth)acryloyloxybutyltrimellitic acid and its anhydride, 4-[2-hydroxy-3-(meth)acryloyloxy]butyltrimellitic acid and its anhydride, 2,3-bis(3,4-dicarboxydibenzoyloxy)propyl (meth)acrylate, N,O-di(meth) acryloyloxytyrosine, O-(meth)acryloyloxytyrosine, N-(meth)acryloyloxytyrosine, N-(meth)acryloyl-p-aminobenzoic acid, N-(meth)acryloyloxy-o-aminobenzoic acid, N-(meth)acryloyl-5-aminosalicylic acid (in case of methacrylate: 5-MASA), N-(meth)acryloyl-4-aminosalicylic acid, 2- or 3- or 4-(meth)acryloyloxybenzoic acid, an addition product of 2-hydroxyethyl (meth)acrylate and pyromellitic dianhydride (in case of methacrylate: PMDM), an addition reaction product of 2-hydroxyethyl (meth)acrylate and maleic anhydride or 3,3',4,4'-benzophenonetetracarboxylic dianhydride (in case of methacrylate: BTDA) or 3,3',4,4'-biphenyltetracarboxylic dianhydride, 2-(3,4-dicarboxybenzoyloxy)-1,3-di(meth)acryloyloxypropane, an adduct of N-phenylglycine or N-triglycine and glycidyl (meth)acrylate, and 4-[(2-hydroxy-3-(meth)acryloyloxypropyl)amino]phthalic acid. These polymerizable monomers having a carboxyl group can be used singly or in combination.

Of the above monomers, 11-methacryloyloxy-1,1-undecanedicarboxylic acid (MAC-10), 4-methacryloyloxyethyltrimellitic acid (4-MET), 4-methacryloyloxyethyltrimellitic anhydride (4-META) and N-methacryloyl-5-aminosalicylic acid (5-MASA) are preferably employed.

Examples of polymerizable monomers having a phosphoric acid group in a molecule include 2-(meth)acryloyloxyethyl acid phosphate, 2- or 3-(meth)acryloyloxypropyl acid phosphate, 4-(meth)acryloyloxybutyl acid phosphate, 6-(meth)acryloyloxyhexyl acid phosphate, 8-(meth)acryloyloxyoctyl acid phosphate, 10-(meth)acryloyloxydecyl acid phosphate, 12-(meth)acryloyloxydodecyl acid phosphate, bis [2-(meth)acryloyloxyethyl]acid phosphate, bis[2- or 3-(meth)acryloyloxypropyl]acid phosphate, 2-(meth)acryloyloxyethylphenyl acid phosphate and 2-(meth)acryloyloxyethyl-p-methoxyphenyl acid phosphate. The phosphoric acid groups in these compounds can be replaced with thiophosphoric acid groups. The polymerizable monomers having a phosphoric acid group or a thiophosphoric acid group can be used singly or in combination.

Of the above compounds, 2-(meth)acryloyloxyethylphenyl acid phosphate and 10-(meth)acryloyloxydecyl acid phosphate are preferably employed.

Examples of polymerizable monomers having a sulfonic acid group in a molecule include 2-methyl-2-(meth)acrylamidopropanesulfonic acid, 2-sulfoethyl (meth)acrylate, 2-(or 1-)sulfo-1-(or -2-)propyl (meth)acrylate, 1-(or 3-)sulfo-2-butyl (meth)acrylate, 3-bromo-2-sulfo-2-propyl (meth)acrylate, 3-methoxy-1-sulfo-2-propyl (meth)acrylate and 1,1-dimethyl-2-sulfoethyl (meth)acrylamide. These polymerizable monomers having a sulfonic acid group can be used singly or in combination.

Of these, 2-methyl-2-(meth)acrylamidopropanesulfonic acid is preferably employed.

All the acid group-containing polymerizable monomers mentioned above can be used singly or in combination.

In the composition of the invention, the polymerizable monomer (C) having an acid group in its molecule is used in an amount of 1 to 10 parts by weight, preferably 2 to 9 parts by weight, particularly preferably 3 to 8 parts by weight, in 100 parts by weight of the total of the polyfunctional polymerizable monomer (A), the monofunctional (meth)acrylate (B) and the polymerizable monomer (C) having an acid group for forming the dental composition of the invention. By the use of the polymerizable monomer (C) having an acid group in its molecule in this amount, the dental adhesive composition of the invention exhibits favorable adhesion properties to adherends.

Examples of the organoboron compounds (D) used as the curing agents in the invention include trialkylboranes, such as triethylborane, tripropylborane, triisopropylborane, tributylborane, tri-sec-butylborane, triisobutylborane, tripentylborane, trihexylborane, trioctylborane, tridecylborane, tridodecylborane, tricyclopentylborane and tricylohexylborane; alkylalkoxyboranes, such as dibutylbutoxyborane; dialkylboranes, such as butyldicyclohexylborane, diisoamylborane and 9-borabicyclo[3.3.1]nonane; aryl borate compounds, such as sodium tetraphenylboron, tetraphenylboron triethanolamine salt, tetraphenylboron dimethyl-p-toluidine salt and tetraphenylboron ethyl dimethylaminobenzoate; and partially oxidized trialkylboranes, such as partially oxidized tributylborane. Of these, tributylborane or partially oxidized tributylborane is preferably employed, and partially oxidized tributylborane is most preferably employed as the organoboron compound.

The organoboron compound that is the component (D) in the composition of the invention is used in an amount of usually 0.5 to 10 parts by weight, preferably 1 to 10 parts by weight, based on 100 parts by weight of the total of the polyfunctional polymerizable monomer (A), the monofunctional (meth)acrylate (B) and the polymerizable monomer (C) having an acid group for forming the dental composition of the invention. In order to favorably balance the working time with the setting time, the organoboron compound (D) is used in the above amount.

To the composition of the invention, an organic peroxide, an inorganic peroxide or an oxidation-reduction metal compound can be added as an auxiliary of the curing agent. Examples of the organic peroxides include diacetyl peroxide, dipropyl peroxide, dibutyl peroxide, dicapryl peroxide, dilauryl peroxide, benzoyl peroxide (BPO), p,p'-dichlorobenzoyl peroxide (CIBPO), p,p'-dimethoxybenzoyl peroxide, p,p'-dimethylbenzoyl peroxide and p,p'-dinitrodibenzoyl peroxide. Examples of the inorganic peroxides include ammonium persulfate, potassium persulfate, potassium chlorate, potassium bromate and potassium perphosphate. Examples of the oxidation-reduction metal compounds include nitrates, chlorides and carboxylates such as acetylacetonate salts of transition metals such as copper, iron and cobalt. Of these, benzoyl peroxide (BPO), p,p'-dichlorobenzoyl peroxide (CIBPO) and copper acetylacetonate are preferable.

The amount of the organic peroxide, the inorganic peroxide or the oxidation-reduction metal compound used as an auxiliary of the curing agent in the invention is 0.01 to 2 times the amount of the organoboron compound that is the component (D).

The filler (E) for use in the invention is not specifically restricted, and publicly known organic fillers, inorganic fillers or inorganic-organic composite fillers are employable.

Examples of the organic fillers preferably used as the filler component (E) in the invention include substantially non-crosslinking (meth)acrylate polymer particles containing not less than 70% by weight of (meth)acrylate units.

Examples of monomers to constitute the (meth)acrylate units include (meth)acrylate monomers, such as methyl (meth)acrylate, ethyl (meth)acrylate, propyl (meth)acrylate, butyl (meth)acrylate, cyclohexyl (meth)acrylate and benzyl (meth)acrylate. Examples of monomers other than the (meth)acrylate monomers include acetic acid vinyl ester, vinylpyrrolidone, maleic anhydride, maleic acid and vinylbenzoic acid. These monomers can be used singly or in combination.

The (meth)acrylate polymer for the invention can be copolymerized with a small amount of a crosslinking monomer when needed. Examples of the crosslinking monomers include polyfunctional monomers, such as ethylene glycol di(meth)acrylate, triethylene glycol di(meth)acrylate and butadiene.

The weight-average molecular weight of the (meth)acrylate polymer particles preferably used as the filler (E) in the invention is in the range of preferably 50000 to 300000.

In the present invention, the above-mentioned organic fillers can be used singly or in combination.

Examples of the inorganic fillers used as the filler component (E) in the invention include metal oxide powders, such as zirconium oxide, bismuth oxide, titanium oxide, zinc oxide and aluminum oxide particles; metal salt powders, such as calcium carbonate, bismuth carbonate, calcium phosphate, zirconium phosphate and barium sulfate; glass fillers, such as silica glass, aluminum-containing glass, barium-containing glass, strontium-containing glass and zirconium silicate glass; fillers having silver slow releasability; and fillers having fluorine slow releasability. These inorganic fillers can be used singly or in combination.

In order to obtain strong bonding between the inorganic filler and the resin, it is preferable to use an inorganic filler having been subjected to surface treatment such as silane treatment or polymer coating.

As the filler (E) for use in the invention, an inorganic-organic composite filler containing the inorganic filler and/or the organic filler is also available.

The organic fillers, the inorganic fillers and the inorganic-organic composite fillers mentioned above can be used singly or in combination.

To decrease a film thickness of the dental adhesive composition and to enhance the restoration effect, the average particle diameter of the above particles is in the range of preferably 0.001 to 30 μm, more preferably 0.01 to 25 μm.

In the composition of the invention, the filler (E) is used in an amount of usually 20 to 300 parts by weight, preferably 30 to 250 parts by weight, based on 100 parts by weight of the total of the polyfunctional polymerizable monomer (A), the monofunctional (meth)acrylate (B) and the polymerizable monomer (C) having an acid group for forming the dental composition of the invention.

The solvent (F) that is optionally used in the dental adhesive composition of the invention is preferably a solvent for common dental use. Examples of such solvents (F) include acetone, methyl ethyl ketone, ethyl acetate, ethanol, propanol and dichloromethane. These solvents can be used singly or in combination.

In the composition of the invention, the solvent (F) is used in an amount of usually 20 to 300 parts by weight, preferably 30 to 250 parts by weight, based on 100 parts by weight of the total of the polyfunctional polymerizable monomer (A), the monofunctional (meth)acrylate (B) and the polymerizable monomer (C) having an acid group for forming the dental composition of the invention.

Further, 0.1 to 5 parts by weight of water may be added, when needed.

To the dental adhesive composition of the invention, a photopolymerization initiator may be added within limits not detrimental to the object of the invention.

As the photopolymerization initiator, one capable of initiating polymerization of a polymerizable monomer upon irradiation with visible light is preferably employed. Examples of such photopolymerization initiators include photosensitizers, specifically, benzoins, such as benzoin, benzoin methyl ether, benzoin ethyl ether and benzoin isopropyl ether; α-diketones, such as benzil, 4,4'-dichlorobenzil, diacetyl, α-cyclohexanedione, d,l-camphorquinone (CQ), camphorquinone-10-sulfonic acid and camphorquinone-10-carboxylic acid; diphenyl monoketones, such as benzophenone, methyl benzoylbenzoate and hydroxybenzophenone; thioxanthones, such as 2,4-diethylthioxanthone and 2-isopropylthioxanthone; and acylphosphine oxides, such as 2,4,6-trimethylbenzoyldiphenylphosphine oxide. These photopolymerization initiators can be used singly or in combination.

In the case where a photopolymerization initiator is used in the dental adhesive composition of the invention, α-diketones, such as benzil, 4,4'-dichlorobenzil, diacetyl peroxide, α-cyclohexanedione, d,l-camphorquinone (CQ), camphorquinone-10-sulfonic acid and camphorquinone-10-carboxylic acid, and acylphosphine oxides are preferable as the photopolymerization initiators. Of these, d,l-camphorquinone, camphorquinone-10-carboxylic acid and 2,4,6-trimethylbenzoyldiphenylphosphine oxide are particularly preferable.

In the case where a photopolymerization initiator is used in the invention, the amount of the photopolymerization initiator added is in the range of 0.1 to 10 parts by weight, preferably 0.2 to 5 parts by weight, based on 100 parts by weight of the organoboron compound.

In order to enhance the polymerization initiation effect of the photopolymerization initiator, it is also possible to use a reducing compound which has no evil influence on the catalytic effect of the organoboron compound, in combination. Examples of such reducing compounds include organic reducing compounds, such as N,N-dimethylaniline, N,N-dimethyl-p-toluidine, N,N-diethyl-p-toluidine, N,N-diethanol-p-toluidine, N,N-dimethyl-p-tert-butylaniline, N,N-dimethylanisidine, N,N-dimethyl-p-chloroaniline, N,N-dimethylaminoethyl (meth)acrylate, N,N-diethylaminoethyl (meth)acrylate, N,N-dimethylaminobenzoic acid and its alkyl esters, N,N-diethylaminobenzoic acid and its alkyl esters, N,N-dimethylaminobenzaldehyde, N-phenylglycine, N-tolylglycine and N,N-(3-methacryloyloxy-2-hydroxypropyl)phenylglycine.

The amount of the reducing compound added is in the range of usually 0.5 to 3.0 times the amount of the photopolymerization initiator used.

To the composition of the invention, other additives may be added within limits not detrimental to the object of the invention. Examples of the additives include germicides, stabilizers, and colorants such as pigments and dyes.

In the dental adhesive composition of the invention, the component (A), the component (B), the component (C), the component (D), the component (E) and the component (F) are preferably packaged separately into two or more packages in an arbitrary combination. Particularly, the component (A), the component (B) and the component (C), which are capable of polymerization, are preferably packaged separately from the component (D) that is a reaction inductive component so that they should not come into contact with the component (D) until just before they are used. Other components are packaged taking the reactivity during storage and transportation into consideration. The components thus packaged separately are mixed just before they are used.

The working time of the dental adhesive composition of the invention needs to be at least 60 seconds after mixing, and the setting time thereof is longer than the working time and not longer than 6 minutes, preferably not longer than 5 minutes. According to the present invention, the working time can be made relatively longer, and besides the curing reaction is completed in an extremely short period of time. Even if the working time and the setting time are thus balanced, the adhesion properties of the dental adhesive composition of the invention are hardly influenced.

EXAMPLES

The present invention is further described with reference to the following examples, but it should be construed that the invention is in no way limited to those examples.

Measurements of Properties

1. Measurement of Curing Rate (Time)

(1) In a mixing dish, 0.18 g of a monomer solution of given composition is placed at room temperature (23° C.). To the monomer solution, 0.014 g (7.8 parts by weight based on 100 parts by weight of the monomer solution) of Super Bond Catalyst (partially oxidized tributylborane, corresponding to the component (D), available from SUN MEDICAL CO., LTD.) is dropwise added, and they are mixed for 2 to 3 seconds by means of an adhesive brush. Immediately thereafter, to the mixture are further added 0.16 g of PMMA polymer particles (polymethyl methacrylate particles, average particle diameter: about 30 μm, corresponding to the component (E), trade name: Super Bond Polymer Powder Clear, available from SUN MEDICAL CO., LTD.), and they are mixed.

(2) The mixture in the mixing dish is poured inside a plastic ring (inner diameter: 10 mm, height: 3 mm) that is placed on a glass plate, and they are transferred into a constant-temperature bath at 37° C. When the end point of curing is approached, the surface of the mixture is lightly pushed with a needle, and a period of time from the addition of the polymer particles to the time the mixture does not adhere to the needle is measured as a setting time.

2. Working Time

In a mixing dish, about 0.09 g of a monomer solution of given composition is placed. To the monomer solution, about 0.007 g (7.8 parts by weight based on 100 parts by weight of the monomer solution) of Super Bond Catalyst (partially oxidized tributylboron, corresponding to the component (D), available from SUN MEDICAL CO., LTD.) is dropwise added, and they are mixed for 2 to 3 seconds by means of an adhesive brush. Immediately thereafter, to the mixture are further added 0.08 g of PMMA polymer particles (polymethyl methacrylate particles, average particle diameter: about 30 μm, corresponding to the component (E), trade name: Super Bond Polymer Powder Clear, available from SUN MEDICAL CO., LTD.), and they are mixed.

The mixture is examined on its viscous state at intervals of 10 seconds, and a period of time from mixing to the time the mixture becomes stringy is measured as a working time.

3. Measurement of Dentin Bond Strength (1) Under water pouring, a mandibular front tooth of bovine is subjected to polishing of 180# to form a flat dentin adhesive surface.

(2) The thus formed dentin adhesive surface is treated with a dentin surface treating agent Green (dental surface treating agent for dentin containing citric acid and ferric chloride as main ingredients, available from SUN MEDICAL CO., LTD.), washed with water and dried. Then, a double-coated tape having a diameter of 4.8 mm is applied to specify an adhesion area.

(3) In a mixing dish, about 0.09 g of a monomer solution of given composition is placed. To the monomer solution, about 0.007 g (7.8 parts by weight based on 100 parts by weight of the monomer solution) of Super Bond Catalyst (partially oxidized tributylboron, corresponding to the component (D), available from SUN MEDICAL CO., LTD.) is dropwise added, and they are mixed by means of an adhesive brush. Immediately thereafter, the mixture is added to PMMA polymer particles (polymethyl methacrylate particles, average particle diameter: about 30 μm, corresponding to the component (E), trade name: Super Bond Polymer Powder Clear, available from SUN MEDICAL CO., LTD.) to prepare a mixed solution/powder material ball, and the ball is applied onto the adhesive surface. Subsequently, an adhesion rod is pressed against the ball to stand the rod thereon.

(4) The thus bonded sample is placed in a constant-temperature constant-humidity bath at 37° C. and humidity of 100%, and after the elapse of a given time (a night), tensile bond strength is measured.

4. Measurement of Enamel Bond Strength (1) Under water pouring, a mandibular front tooth of bovine is subjected to polishing with a piece of waterproof abrasive paper 1000# to form a flat enamel adhesive surface.

(2) The thus formed enamel adhesive surface is treated with an enamel surface treating agent Red (dental surface treating agent for enamel containing a phosphoric acid aqueous solution as a main ingredient, available from SUN MEDICAL CO., LTD.), washed with water and dried. Then, a double-coated tape is applied to specify an adhesion area having a diameter of 4.8 mm.

(3) The same procedure as in the step (3) of the measurement 3 is carried out.

(4) The thus bonded sample is placed in a constant-temperature constant-humidity bath at 37° C. and humidity of 100%. After the elapse of 20 hours, the sample is transferred into a thermal cycle test machine of 5° C./55° C. and subjected to 3000 thermal cycles, followed by measuring tensile bond strength.

5. Measurement of Metal Bond Strength (1) A gold/silver/palladium alloy plate of 1 cm square and about 2 mm thickness is sandblasted, cleaned and dried. Then, a double-coated tape having a diameter of 4.8 mm is applied to specify an adhesion area.

(2) The thus treated alloy plate is treated with a metal surface treating agent V-Primer (metal surface treating agent, available from SUN MEDICAL CO., LTD.).

(3) The same procedure as in the step (3) of the measurement 3 is carried out.

(4) The thus bonded sample is placed in a constant-temperature constant-humidity bath at 37° C. and humidity of 100%. After the elapse of 20 hours, the sample is transferred into a thermal cycle test machine of 5° C./55° C. and subjected to 5000 thermal cycles, followed by measuring tensile bond strength.

Example 1

A monomer solution (corresponding to the component (A)+the component (B)+the component (C)) consisting of 3.5 parts by weight of glycerol dimethacrylate (GDMA), 5 parts by weight of 4-methacryloyloxyethyltrimellitic acid (4-MET) and 91.5 parts by weight of methyl methacrylate (MMA) was prepared. Then, setting time, working time and bond strengths to dentin, enamel and metal were measured in the same manner as in the aforesaid measurements of properties. The results are set forth in Table 1.

Examples 2-5

A monomer solution (corresponding to the component (A)+the component (B)+the component (C)) was prepared in the same manner as in Example 1, except that the amount of 4-methacryloyloxyethyltrimellitic acid (4-MET) was set to 5 parts by weight, the total amount of glycerol dimethacrylate (GDMA) and methyl methacrylate (MMA) was changed to 95 parts by weight, and the amount of GDMA was changed as shown in Table 1. Then, setting time, working time and bond strengths to dentin, enamel and metal were measured in the same manner as in Example 1. The results are set forth in Table 1.

Example 6

A monomer solution (corresponding to the component (A)+the component (B)+the component (C)) was prepared in the same manner as in Example 1, except that tetramethylolmethane triacrylate (TMM-T) was used instead of glycerol dimethacrylate (GDMA). Then, setting time, working time and bond strengths to dentin, enamel and metal were measured in the same manner as in Example 1. The results are set forth in Table 1.

Comparative Example 1

A monomer solution (corresponding to the component (B) and the component (C)) was prepared in the same manner as in Example 1, except that glycerol dimethacrylate (GDMA) was not used and the amount of methyl methacrylate (MMA) was changed to 95 parts by weight. Then, setting time, working time and bond strengths to dentin, enamel and metal were measured in the same manner as in Example 1. The results are set forth in Table 1.

TABLE 1

| | Composition (part(s) by weight) | | | Curing time | Pot life | Bond strength (MPA) | | |
|---|---|---|---|---|---|---|---|---|
| | (B) | (C) | (A) | (minute(s):second(s)) | (second(s), 20° C.) | Dentin | Enamel | Metal |
| | MMA | 4-MET | GDMA | — | — | — | — | — |
| Ex. 1 | 91.5 | 5 | 3.5 | 4:40 | 60 | 20.9 | 11.9 | 27.7 |
| Ex. 2 | 85 | 5 | 10 | 3:00 | 70 | 15.7 | 13.8 | 19.0 |
| Ex. 3 | 80 | 5 | 15 | 2:25 | 70 | 14.7 | 15.0 | 24.7 |
| Ex. 4 | 75 | 5 | 20 | 2:15 | 75 | 12.4 | 15.5 | 17.6 |
| Ex. 5 | 65 | 5 | 30 | 2:00 | 60 | 10.5 | 14.6 | 16.1 |
| Ex. 6 | MMA 91.5 | 4-MET 5 | TMM-T 3.5 | 5:00 | 60 | 19.8 | 10.4 | 33.3 |
| Comp. Ex. 1 | MMA 95 | 4-MET 5 | — | 7:00 | 60 | 17 | 15.4 | 26 |

What is claimed is:

1. A dental adhesive composition comprising:
   (A) a polyfunctional polymerizable monomer selected from the group consisting of glycerol dimethacrylate and tetramethylolmethane triacrylate, in an amount of 1 to 30 parts by weight,
   (B) a monofunctional (meth)acrylate having no hydroxyl group in an amount of 65 to 95 parts by weight,
   (C) a polymerizable monomer having an acid group, in an amount of 1 to 10 parts by weight, and
   (D) an organoboron compound in an amount of 0.5 to 10 parts by weight based on 100 parts by weight of the total of the polyfunctional polymerizable monomer (A), the monofunctional (meth)acrylate (B) and the polymerizable monomer (C) having an acid group,
   with the proviso that the total of the component (A), the component (B) and the component (C) is 100 parts by weight.

2. The dental adhesive composition as claimed in claim 1, further comprising a filler (E) in an amount of 20 to 300 parts by weight based on 100 parts by weight of the total of the component (A), the component (B) and the component (C).

3. The dental adhesive composition as claimed in claim 1, further comprising a solvent (F) in an amount of 10 to 200 parts by weight based on 100 parts by weight of the total of the component (A), the component (B) and the component (C).

4. The dental adhesive composition as claimed in claim 1, wherein the polyfunctional polymerizable monomer (A) is contained in an amount of 1 to 20 parts by weight.

5. The dental adhesive composition as claimed in claim 1, wherein the polyfunctional polymerizable monomer (A) is glycerol dimethacrylate.

6. The dental adhesive composition as claimed in claim 1, wherein the polymerizable monomer (C) having an acid group is 4-methacryloyloxyethyltrimellitic acid and/or 4-methacryloyloxyethyltrimellitic anhydride.

7. The dental adhesive composition as claimed in claim 1, wherein the organoboron compound (D) is tributylborane and/or a partial oxide thereof.

8. The dental adhesive composition as claimed in claim 2, wherein the filler (E) is polymethyl (meth)acrylate particle.

9. The dental adhesive composition as claimed in claim 2, wherein the polyfunctional polymerizable monomer (A) is contained in an amount of 1 to 20 parts by weight.

10. The dental adhesive composition as claimed in claim 2, wherein the polyfunctional polymerizable monomer (A) is glycerol dimethacrylate.

11. The dental adhesive composition as claimed in claim 2, wherein the polymerizable monomer (C) having an acid group is 4-methacryloyloxyethyltrimellitic acid and/or 4-methacryloyloxyethyltrimellitic anhydride.

12. The dental adhesive composition as claimed in claim 2, wherein the organoboron compound (D) is tributylborane and/or a partial oxide thereof.

13. A dental adhesive composition comprising:
   (A) a polyfunctional polymerizable monomer selected from the group consisting of glycerol dimethacrylate and tetramethylolmethane triacrylate, in an amount of 1 to 30 parts by weight,
   (B) at least one monofunctional (meth)acrylate having no hydroxyl group selected from the group consisting of alkyl (meth)acrylates, (poly)alkylene glycol monoalkyl ether (meth)acrylates, fluoroalkyl esters of (meth)acrylic acids, silane compounds having (meth)acryloxyalkyl groups, and (meth)acrylates having heterocyclic rings, in an amount of 65 to 95 parts by weight,
   (C) a polymerizable monomer having an acid group, in an amount of 1 to 10 parts by weight, and
   (D) an organoboron compound in an amount of 0.5 to 10 parts by weight based on 100 parts by weight of the total of the polyfunctional polymerizable monomer (A), the monofunctional (meth)acrylate (B) and the polymerizable monomer (C) having an acid group,
   with the proviso that the total of the component (A), the component (B) and the component (C) is 100 parts by weight.

14. The dental adhesive composition as claimed in claim 13, further comprising a filler (E) in an amount of 20 to 300 parts by weight based on 100 parts by weight of the total of the component (A), the component (B) and the component (C).

15. The dental adhesive composition as claimed in claim 13, further comprising a solvent (F) in an amount of 10 to 200 parts by weight based on 100 parts by weight of the total of the component (A), the component (B) and the component (C).

16. The dental adhesive composition as claimed in claim 13, wherein the polymerizable monomer (C) having an acid group is 4-methacryloyloxyethyltrimellitic acid and/or 4-methacryloyloxyethyltrimellitic anhydride.

* * * * *